United States Patent [19]

Radin et al.

[11] Patent Number: 4,845,997

[45] Date of Patent: Jul. 11, 1989

[54] SELF-ALIGNMENT GRIP FOR MECHANICAL TESTING

[75] Inventors: Alexander Radin, Cherry Hill, N.J.; Zhirui Wang, Philadelphia, Pa.

[73] Assignee: Trustees of the University of Pennsylvania, Philadelphia, Pa.

[21] Appl. No.: 157,328

[22] Filed: Feb. 17, 1988

[51] Int. Cl.$^4$ ............................................. G01N 3/02
[52] U.S. Cl. ......................................... 73/831; 73/856
[58] Field of Search ................................. 73/856–860, 73/826, 827, 828, 830, 831, 833, 834, 818, 821, 825; 279/1 J, 1 L, 1 TE; 269/139

[56] References Cited

U.S. PATENT DOCUMENTS

| | | | |
|---|---|---|---|
| 2,487,022 | 11/1949 | Placa | 269/139 |
| 3,005,336 | 10/1961 | Wyman | 73/860 |
| 3,107,524 | 10/1963 | O'Connor | 73/860 |
| 4,666,353 | 5/1987 | Micek | 279/1 J |
| 4,721,000 | 1/1988 | Scanlon | 73/833 |

FOREIGN PATENT DOCUMENTS

| | | | |
|---|---|---|---|
| 260942 | 5/1970 | U.S.S.R. | 73/860 |
| 448130 | 6/1936 | United Kingdom | 73/860 |

OTHER PUBLICATIONS

MTS Brochere, Model 640.05, Feb. 1965.
MTS Brochere, Model 640.04, Feb. 1965.
MTS Systems Corporation, Grips and Fixtures Catalog 300024-13/640.0305, MTS Systems Corporation, Box 24012, Minneapolis, Minn, 55424.
Trade Literature for *Instron Series 2742*, publication PS-6-1088, Instron Corporation, 100 Royall St, Canton, Mass, 02021.
Trade Literature for *Instron Series 2718*, publication IC-6-66(A), Instron Corporation, 100 Royall St, Canton, Mass, 02021.
Z. Wang, *Fatigue Behavior of 70–30 Alpha Brass: Pauschinger Effect and Surface Behavior in Single Crystals and High Cycle Fatigue Crack Formation at Twin Bounderies*, Doctoral disertation, Polytechnic Institute of New York, Jan., 1986, Microfilm recording at University Microfilms, 30 M. Zeeb Rd., Ann Arbor, Mich. 48106.

Primary Examiner—Stewart J. Levy
Assistant Examiner—Robert R. Raevis
Attorney, Agent, or Firm—Woodcock Washburn Kurtz Mackiewicz & Norris

[57] ABSTRACT

A novel mechanical testing grip is disclosed which accounts for both eccentricity between the load cell and cross head, as well as machining tolerances in the specimen. The device includes a ball and socket joint disposed between two alignment members and secured by connecting members. The connecting members have curved elements for contacting correspondingly curved apertures of the alignment members so that substantially no extra force is exerted upon the test specimen. The grip does not require any heating or excessive waiting periods prior to conducting a mechanical test and can reduce the misalignment of a mechanical test specimen below about 0.02° from the load axis.

10 Claims, 3 Drawing Sheets

SELF-ALIGNMENT GRIP FOR MECHANICAL TESTING

FIELD OF THE INVENTION

This invention relates to the alignment of specimens in mechanical testing machines, and particularly, to alignment devices having self-aligning specimen grips.

BACKGROUND OF THE INVENTION

It is generally known that any mechanical testing machine has some eccentricity between its load cell and the cross-head. It is also known that the machining tolerances associated with the preparation of test bars often provides an imperfect geometry which can adversely affect the testing results. Most testing grips used to clamp specimens usually cannot allow any adjustment to correct the unavoidable misalignment due to the aforementioned factors. Despite this, the current trend in holding devices appears to be directed toward the facilitation of specimen installation through the use of hydraulic grips rather than the minimization of alignment errors. See in this regard *MTS Systems Corporation, Grips and Fixtures Catalog,* 300024-13/640.0305, MTS Systems Corporation, Box 24012, Minneapolis, Minn. 55424 and Trade Literature for the INSTRON Series 2742 and 2718, publications PS- 6-1088 and IC-6-66 (A), Instron Corporation, 100 Royall Street, Canton, Mass. 02021.

One popularly employed device, used often with single crystals where misalignment can cause unreliable measurements, is the WOOD ALLOY Grip System, whereby a set of alignment grips is connected to an alloy pot comprising molten metal. The grips are free to align with the specimen when the device is hot, but a cooling period of approximately 30 minutes to one hour is required prior to testing.

While this device has been popular, some testing problems have been associated with its use. With a heavy WOOD alloy pot on the top, the specimen can't really be freely aligned. The final alignment depends on the machining quality of the specimen grip part. Additionally, when connecting the WOOD ALLOY pot to a load cell of a mechanical testing machine, the cell will be heated up, resulting in considerable shifting of the load signal. Accordingly, an extended period of time is required to let the load cell cool down so that an accurate reading can be taken. Finally, the alignment of this device becomes unadjustable once the WOOD ALLOY solidifies.

Alternatively, at least one mechanical aligner has been introduced recently to overcome the heat-generated side effects caused by the WOOD ALLOY Grip. Z. Wang, *Fatigue Behavior of 7030 Alpha Brass: Pauschinqer Effect and Surface Behavior in Single Crystals and High Cycle Fatigue Crack Formation at Twin Boundaries,* Doctoral dissertation, Polytechnic Institute of New York, January, 1986, Microfilm recording at: University Microfilms, 30 M. Zeeb Road, Ann Arbor, Mich. 48106. This dissertation discloses a top grip body including a self-alignment hemisphere and a pair of specimen stoppers. The device also includes a bottom grip, configured similarly to the top grip, and including a hemispherical cavity. This device provides very little mobility to its flange portions, and thus, full employment of the mobility offered by the spherical center portion is impaired. In addition, torque may be created by the impingement of the flat portions of the bolts and nuts against the flanges which can render the reading unacceptable.

It is known that a misalignment of about 3° from the axis of a tensile load on a half inch gage length specimen can produce unacceptable stress-strain information for objects such as soft, single crystal specimens. Moreover, a misalignment of only about 1° off the axis of the tensile load can provide a misreading in the stress-strain curve of polymer specimens. Accordingly, there is a need for a mechanical testing alignment and gripping device that can provide for less than 1° of misalignment. There is also a need for a faster alignment device that does not result in load cell heating with attendant inconvenience and reading inaccuracies.

SUMMARY OF THE INVENTION

This invention provides a novel gripping device having a pair of alignment members connected about a central ball and socket joint and secured to provide increased alignment flexibility to the gripping device. The resulting alignment can overcome cross head and load cell eccentricities and machining inaccuracies in specimens. The upper part of this self-aligning grip is typically connected to the machine load cell and the lower part is typically connected to the specimen. Between the two parts, a preferred hardened steel ball is disposed for transferring load from one part to the other. The two parts of this grip are held together by preferred nuts and bolts having hemispherical heads which allow the two parts of the grip to be adjusted according to the machine and specimen conditions. Since the tightening of these bolts will not apply any extra force to the specimen, the device can reduce the misalignment of the specimen below 0.1°, preferably below 0.05°, and most preferably below about 0.02° from the load axis. Accordingly, a more accurate mechanical testing grip is provided. The device overcomes prior art problems associated with load cell heating and waiting periods. The alignment device, moreover, avoids unnecessary torques in the specimen which can have adverse impact on the mechanical testing results.

It is therefore, an object of this invention to provide a self-alignment mechanical testing grip which can provide truer alignment of the specimen.

It is another object of this invention to provide a mechanical testing alignment grip which can be easily employed within relatively short period of time.

It is a further object of this invention to provide a mechanical testing alignment grip that can account for both eccentricity between the load cell and cross head, as well as machining tolerances in the specimen.

With these and other objects in view, this invention resides in the novel construction, combination, arrangement of parts and methods substantially as hereinafter described and more particularly defined by the attached claims.

BRIEF DESCRIPTION OF THE DRAWINGS

The accompanying drawings illustrate a complete embodiment of the invention according to the best mode so far devised for the practical application of the principles thereof, and in which.

DETAILED DESCRIPTION OF THE INVENTION

Figure 1:
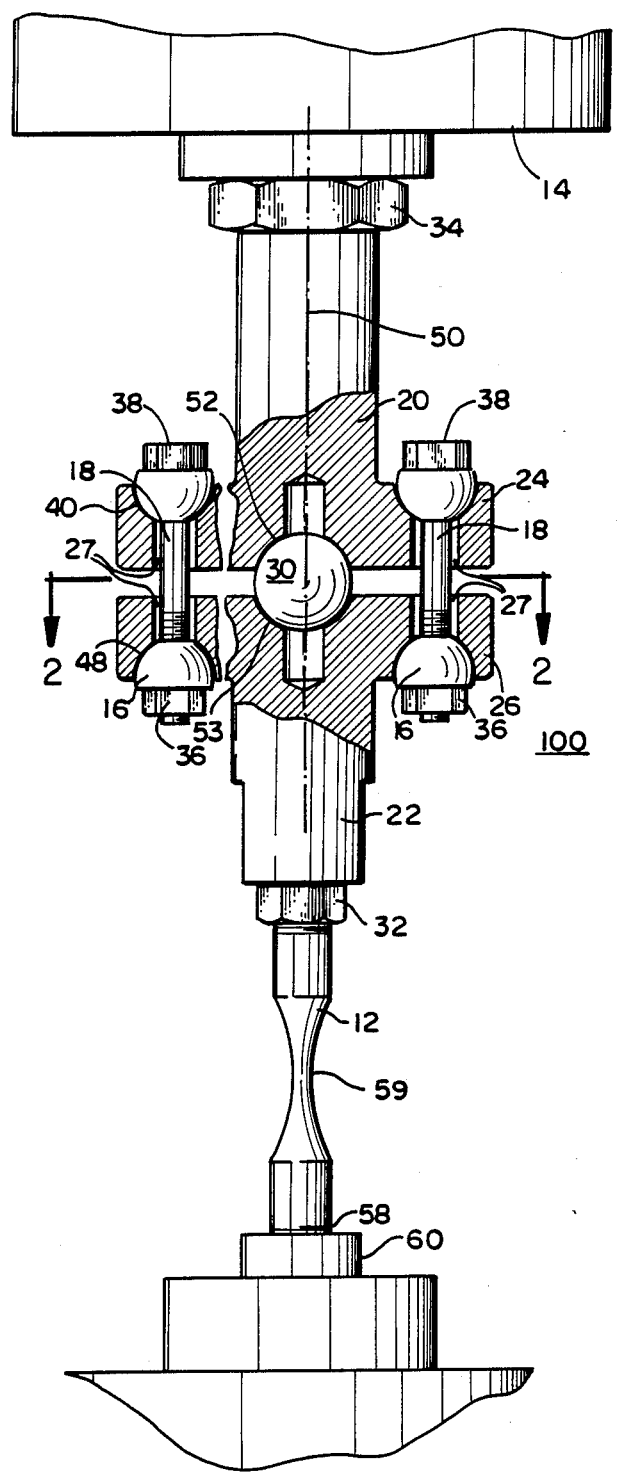
FIG. 1 is a transverse view of a mechanical testing grip in accordance with a preferred embodiment of this invention, illustrating, in partial cross-section, inner elements of the alignment device.

The present invention provides novel gripping devices for holding mechanical testing specimens. These devices include first and second alignment members having a generally common axis. These members include a plurality of apertures disposed therethrough, which are located outwardly from the generally common axis. One of the alignment members also includes holding means for gripping the mechanical testing specimen. In further accordance with this invention, ball and socket means are disposed between the first and second alignment members along the generally common axis for transferring an alignment load between the members. As used herein, the term "alignment load" refers to the force exerted when the connecting members are tightened and the alignment members are compressed against the ball and socket means. It is assumed that the ball and socket means could similarly transfer compressive loads, for example, during fatigue and compressive loading tests.

The invention includes a plurality of connecting members for connecting the first and second alignment members. Each of these connecting members is disposed between an aperture in the first alignment member and a corresponding aperture in the second alignment member. The apertures and the connecting members include interfacing curved surfaces so that the alignment members are free to move relative to one another to perfect the alignment.

The alignment members of this invention can include flanges extending outwardly from the generally common axis. It is also preferred that the alignment members include depressions, preferably having spherically concave configurations, disposed at the members' ends and axially aligned with the generally common axis.

In one preferred embodiment the ball and socket means includes a hardened steel ball, i.e. AISI 4340 ($R_c48$), which is disposed to slide against the central depressions of the alignment members, thus forming a ball and socket joint. In another preferred embodiment, the connecting members include bolts and nuts having hemispherical heads, which are disposed to compress against the flanges of the alignment members. More preferably, these hemispherical heads are disposed within spherical receiving portions of the apertures such that they can be tightened without applying any substantial force to the mechanical testing specimen. The device may also include a threaded portion within the holding means for holding mechanical testing specimens and a threaded attachment means for attaching the device to a load cell of a mechanical testing machine. It is envisioned that both three and four bolt configurations could be devised for the novel devices of this invention. Moreover, it is expected that the apertures can comprise a bore having an elongated transverse cross-section for permitting a relative rotating motion between the first and second alignment members. Finally, the great degree of accuracy produced by this gripping instrument makes it ideal for mechanically testing single crystals.

Referring now to the figures, and particularly to FIG. 1, a gripping device 100 for holding a mechanical testing specimen 12 is disclosed. The device 100 comprises first and second alignment members 20 and 22 having a generally common axis 50. Each of these members 20 and 22 includes a plurality of apertures 27 disposed therethrough and located outwardly from said generally common axis 50. At least one of the alignment members 20 and 22 incorporates a holding means for gripping the mechanical testing specimen 12. The device 100 has ball and socket means disposed between the first and second alignment members 20 and 22 along the generally common axis 50 for transferring an alignment load between the members 20 and 22. The device 100 further includes a plurality of connecting members for connecting the first and second alignment members 20 and 22. Each of the connecting members is disposed between an aperture 27 in the first alignment member 20 and a corresponding aperture in the second alignment member 22. Each of these apertures 27 and the connecting members includes an interfacing curved surface.

In a preferred embodiment of this invention, the first and second alignment members 20 and comprise flanges 24 and 26 extending outwardly from the generally common axis 50. Also along this axis, are preferred depressions 52 and 53, which preferably comprise a spherically concave configuration.

The preferred ball and socket arrangement of this invention includes a hardened steel ball 30 which is disposed to transfer at least the alignment load from one member 20 to the other 22. Preferably this hardened steel ball 30 is disposed within the depressions 52 and 53 of the alignment members 20 and 22.

Figure 3:
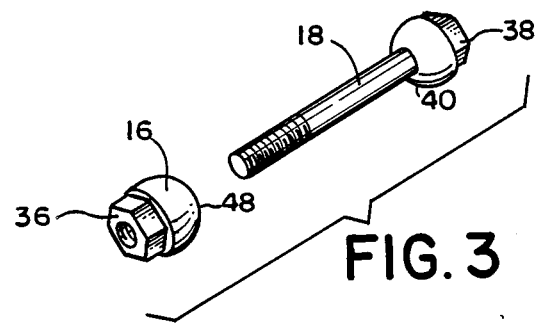
FIG. 3 is an exploded view of a preferred bolt and nut combination having hemispherical heads thereon.

The preferred connecting members of this invention, accordingly to FIG. 3, include bolts 18 having hemispherical heads 40. The bolts preferably include hemispherical headed nuts 16 having hexagonal ends 36 and hemispherical heads 48. In the most preferred configuration, the hemispherical heads 40 and 48 of the bolts 18 and nuts 16 are disposed to compress against flanges 24 and 26. In this embodiment, the apertures 27 include spherical receiving portions for engaging the hemispherical heads 40 and 48 of the bolts 18 and nuts 16, thus the spherical receiving portions of the apertures 27 and the hemispherical heads 40 and 48 may be referred to as interfacing curved surfaces. As depicted in FIG. 1, when the spheric bolts 18 and nuts 16 are tightened, no substantial extra force is exerted on the specimen 12. This feature, as well as others, enables the device to reduce any misalignment of the specimen below 1°, to below 0.1°, preferably below about 0.05°, and most preferably below about 0.02°.

Figure 2:
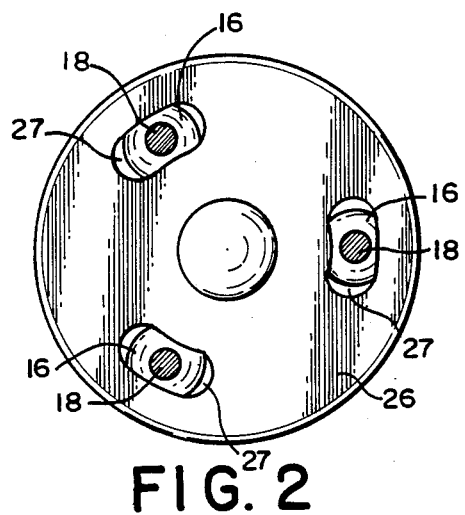
FIG. 2 is a end-view, taken from cross-section line 2—2 of FIG. 1, illustrating preferred hemispherical nuts disposed in the apertures of the lower alignment member.
Figure 4:
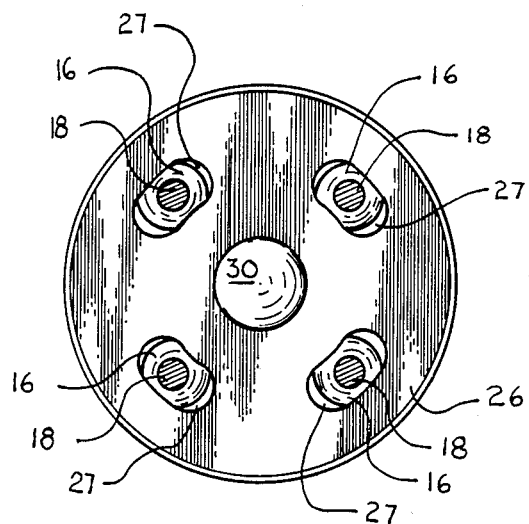
FIG. 4 is an end-view of an alternative mechanical testing grip embodiment, illustrating four hemispherical nuts disposed in four apertures of the lower alignment member.

Other aspects of this embodiment include a threaded portion disposed within the holding means 32 of the alignment member 22 for holding a mechanical testing specimen 12. It is expected that hydraulic-grips, as previously discussed, could be used for this purpose. The device 100 can further include a threaded attachment means 34 for attaching the device to a load cell 14 of a mechanical testing machine. It is expected that the apertures 27 could also comprise a bore having an elongated transverse crosssection, as substantially described in FIG. 2 and FIG. 4, for permitting a relative rotation motion between the first and second alignment members 20 and 22.

An example of a mechanical testing procedure using the preferred embodiment will now be described. First, the mechanical testing specimen 12 is inserted into threaded attachment means 32 and slightly tightened. Next a dial indicator with a magnetic base is applied to the specimen at a location between the gauge part 59 and the specimen holding part 58. The cross-head is then motioned up and down and a reading of misalignment is taken. The bolts 18 are then tightened, and if too large a misalignment is found, these bolts can be adjusted until the misalignment is about 0.00 cm/cm. After tightening the bolts 18, the dial indicator is removed and the lower grip is applied to the specimen and tightened until it receives a 3 to 5 Kg compressive load from the mechanical testing machine actuator. Once a good alignment is obtained, the specimen can be tightened and started under either a load control or strain control setting of the mechanical testing machine.

From the foregoing it can be realized that this invention provides improved mechanical testing grips providing truer alignment without heating the load cell. The device as described herein accounts for both eccentricity between the load cell and cross head, as well as machining tolerances in the specimen, to provide for greater accuracy in mechanical testing. Although various embodiments have been illustrated, this was for the purpose of describing, but not limiting, the invention. Various modifications, which will become apparent to one skilled in the art, are within the scope of this invention described in the attached claims.

We claim:

1. A gripping device for holding a mechanical testing specimen, comprising:
   (a) first and second alignment members having a generally common axis, each of said members comprising a flange extending outwardly from said generally common axis, said flanges having a plurality of apertures disposed therethrough and located outwardly from said generally common axis, one of said alignment members having holding means for gripping said mechanical testing specimen, said first and second alignment members comprising ball and socket means disposed along said generally common axis for transferring at least an alignment load between said members, each of said first and second alignment members further including a depression at one end of each of said members, said depressions axially aligned with said generally common axis of said first and second alignment members for receiving the ball portion of said ball and socket means, said depressions having a spherically concave configuration; and
   (b) a plurality of connecting members for connecting said first and second alignment members, each of said connecting members being disposed between an aperture in the first alignment member and a corresponding aperture in the second alignment member, each of said apertures and said connecting members having interfacing curved surfaces; each of said apertures further comprising a bore having an elongated transverse cross-section for permitting a relative rotation between said first and second alignment members.

2. The device of claim 1 wherein said connecting members comprise three bolts.

3. The device of claim 1 wherein said connecting members comprise four bolts.

4. The device of claim 1 wherein said connecting members comprises a bolt.

5. The device of claim 4 wherein each of said connecting members further comprises at least one nut, said nuts and bolts having hemispherical head for securing together said first and second alignment members.

6. The device of claim 5 wherein said hemispherical heads of said bolts and nuts are disposed to compress against said flanges.

7. The device of claim 6 wherein said hemispherical heads of said bolts and nuts are disposed to compress against said flanges.

8. The device of claim 7 wherein said hemispherical heads of said bolts and nuts are disposed so as not to apply excess substantial force to said mechanical testing specimen.

9. The device of claim 7 wherein said holding means comprises threaded portion for holding said mechanical testing specimen.

10. The device of claim 7 wherein said first alignment member comprises threaded attachment means for attaching said device to a load cell of a mechanical testing machine.

* * * * *